US011044945B2

(12) United States Patent
Nakano et al.

(10) Patent No.: US 11,044,945 B2
(45) Date of Patent: Jun. 29, 2021

(54) FLAVOR INHALER, CARTRIDGE, AND FLAVOR UNIT

(71) Applicant: JAPAN TOBACCO INC., Tokyo (JP)

(72) Inventors: Takuma Nakano, Tokyo (JP); Akihiko Suzuki, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 348 days.

(21) Appl. No.: 16/241,570

(22) Filed: Jan. 7, 2019

(65) Prior Publication Data

US 2019/0133198 A1    May 9, 2019

Related U.S. Application Data

(63) Continuation of application No. PCT/JP2016/072063, filed on Jul. 27, 2016.

(51) Int. Cl.
*A24F 47/00* (2020.01)
*A24F 40/53* (2020.01)
(Continued)

(52) U.S. Cl.
CPC .............. *A24F 40/53* (2020.01); *A24F 40/30* (2020.01); *A24F 40/485* (2020.01); *A24F 40/50* (2020.01);
(Continued)

(58) Field of Classification Search
CPC ................................ A24F 40/50; A24F 40/53
(Continued)

(56) References Cited

U.S. PATENT DOCUMENTS 7,726,320 B2 * 6/2010 Robinson ................ A24F 40/42
                                                            131/200
10,010,695 B2 * 7/2018 Buchberger ......... A61M 11/041
(Continued)

FOREIGN PATENT DOCUMENTS

EP    2 617 303 A1    7/2013
EP    2 989 912 A1    3/2016
(Continued)

OTHER PUBLICATIONS

International Search Report (PCT/ISA/210) issued in PCT/JP2016/072063, dated Oct. 11, 2016.
(Continued)

*Primary Examiner* — Neil Abrams
(74) *Attorney, Agent, or Firm* — Birch, Stewart, Kolasch & Birch, LLP

(57) ABSTRACT

Provided is a flavor inhaler comprising: an atomizing unit that generates an aerosol from an aerosol source; a flavor source provided downstream from the atomizing unit; a mouthpiece section provided downstream from the flavor source; a control unit that controls the atomizing unit; an aerosol flow path leading to the mouthpiece section from the atomizing unit; and an information source for holding identification information associated with a correction value for correcting a reference aerosol amount that is the amount of aerosol generated by the atomizing unit and that is an amount designed in advance. The aerosol flow path branches between the atomizing unit and the flavor source into a first branch flow path through which the flavor source passes and a second branch flow path that differs from the first branch flow path. The correction value is a value relating to a flow rate ratio that is the flow rate in the first branch flow path relative to a predetermined flow rate when the mouthpiece section is sucked at a predetermined flow rate. The control unit controls the atomizing unit on the basis of a target (Continued)

aerosol amount calculated on the basis of the reference aerosol amount and the correction value.

27 Claims, 8 Drawing Sheets

(51) Int. Cl.
*A24F 40/30* (2020.01)
*A24F 40/485* (2020.01)
*A24F 40/50* (2020.01)
*A24F 40/65* (2020.01)
*A61M 11/00* (2006.01)
*A61M 15/00* (2006.01)
*A61M 15/06* (2006.01)
*A24F 40/10* (2020.01)
*A24F 40/20* (2020.01)

(52) U.S. Cl.
CPC .......... *A24F 40/65* (2020.01); *A61M 11/001* (2014.02); *A61M 15/002* (2014.02); *A61M 15/06* (2013.01); *A24F 40/10* (2020.01); *A24F 40/20* (2020.01); *A61M 15/0021* (2014.02)

(58) Field of Classification Search
USPC .......................................................... 131/329
See application file for complete search history.

(56) References Cited

U.S. PATENT DOCUMENTS

| | | | |
|---|---|---|---|
| 10,117,460 B2* | 11/2018 | Sears ...................... | A24F 40/40 |
| 10,881,143 B2* | 1/2021 | Suzuki .................... | A24F 47/00 |
| 10,912,333 B2* | 2/2021 | Atkins ................ | A61M 11/042 |
| 2008/0092912 A1 | 4/2008 | Robinson et al. | |
| 2016/0106936 A1 | 4/2016 | Kimmel | |
| 2019/0133198 A1* | 5/2019 | Nakano ................ | A24F 47/008 |

FOREIGN PATENT DOCUMENTS

| | | |
|---|---|---|
| JP | 2010-506594 A | 3/2010 |
| WO | WO 2014/110119 A1 | 7/2014 |
| WO | WO 2014/115324 A1 | 7/2014 |

OTHER PUBLICATIONS

Eurasian Office Action for corresponding Eurasian Application No. 201990377, dated Mar. 19, 2020, with English translation.

* cited by examiner

Fig. 4

Obtaining a correction value (a flow rate ratio β) — S101

Determining a target amount of aerosol based on the reference amount of aerosol and the flow rate ratio β — S102

Controlling the atomizing section based on the target amount of aerosol — S103

Fig. 7

```
            ↓
┌─────────────────────────────┐
│ Calculating an accumulated  │
│ value of amounts of aerosol │──S702
│ generated in the atomizing  │
│ section                     │
└─────────────────────────────┘
            ↓
┌─────────────────────────────┐
│ Calculating an accumulated  │
│ value of amounts of aerosol │──S704
│ passed through the first    │
│ branched flow path          │
└─────────────────────────────┘
            ↓
         ◇ Accumulated value
   NO ← of amounts of generated aerosol ──S706
         > First threshold ?
            ↓ YES
┌─────────────────────────────┐
│ Changing the amount of      │
│ aerosol to be generated in  │──S708
│ the atomizing section       │
└─────────────────────────────┘
            ↓
         ◇ Accumulated value
   NO ← of amounts of generated aerosol ──S710
         > Second threshold ?
            ↓ YES
┌─────────────────────────────┐
│ Stopping supply of electric │
│ power to the atomizing unit │──S712
└─────────────────────────────┘
```

FLAVOR INHALER, CARTRIDGE, AND FLAVOR UNIT

CROSS REFERENCE TO RELATED APPLICATIONS

This application is a continuation of international application No. PCT/JP2016/072063, filed on Jul. 27, 2016.

TECHNICAL FIELD

The present invention relates to a flavor inhaler, and a cartridge and a flavor unit which are components of the flavor inhaler.

BACKGROUND ART

A type of flavor inhaler, by which flavor is inhaled without a burning process, has been known. A flavor inhaler comprises an atomizing unit for atomizing an aerosol source without a burning process, and a flavor source (for example, a tobacco source) arranged in a position closer to a mouthpiece side than a position of the atomizing unit (for example, refer to Patent Literature 1).

CITATION LIST

Patent Literature

PTL 1: Japanese Patent Application Public Disclosure No. 2010-506594

SUMMARY OF INVENTION

The gist of a first characteristic is that a flavor inhaler comprises: an atomizing section for generating aerosol from an aerosol source; a flavor source positioned downstream the atomizing section; a mouthpiece section positioned downstream the flavor source; a control section for controlling the atomizing section; an aerosol flow path leading from the atomizing section to the mouthpiece section; and an information source for holding identification information associated with a correction value used for correcting a reference amount of the aerosol that is a amount of the aerosol to be generated in the atomizing section and is designed in advance; wherein the aerosol flow path is divided, in a part between the atomizing section and the flavor source, into a first branched flow path passing through the flavor source and a second branched flow path different from the first branched flow path; the correction value is a value relating to a flow rate ratio of a flow rate in the first branched flow path to a predetermined flow rate at the time when the mouthpiece section is sucked at the predetermined flow rate; and the control section controls the atomizing section based on a target amount of the aerosol that is calculated based on the reference amount of the aerosol and the correction value.

The gist of a second characteristic is that the second characteristic comprises the first characteristic, wherein, in the case that the flow rate ratio is larger than a pre-designed value, the target amount of the aerosol is set to be smaller than a target amount of the aerosol in the case that the flow rate ratio coincides with the pre-designed value; and, in the case that the flow rate ratio is smaller than the pre-designed value, the target amount of the aerosol is set to be larger than the target amount of the aerosol in the case that the flow rate ratio coincides with the pre-designed value.

The gist of a third characteristic is that the third characteristic comprises the first characteristic or the second characteristic, wherein the first branched flow path and the second branched flow path are merged with each other in a point downstream the flavor source.

The gist of a fourth characteristic is that the fourth characteristic comprises one of the first to third characteristics, wherein the control section controls supply of electric energy to the atomizing section.

The gist of a fifth characteristic is that the fifth characteristic comprises the fourth characteristic, wherein the atomizing section comprises a resistance heating element, and electric energy supplied to the resistance heating element per a single puff action is represented by E, characteristic parameters of the atomizing section are represented by a and b, a amount of the aerosol generated per a single puff action is represented by A, and the control section calculates the amount A of the aerosol by use of formula $A=a*E+b$.

The gist of a sixth characteristic is that the sixth characteristic comprises the fourth characteristic or the fifth characteristic, wherein the atomizing section comprises a resistance heating element, and the target amount of the aerosol is represented by $A_T$, target electric energy that should be supplied to the resistance heating element per a single puff action is represented by $E_T$, characteristic parameters of the atomizing section are represented by a and b, and the control section determines the electric energy $E_T$ that should be supplied to the resistance heating element by use of formula $E_T=(A_T-b)/a$.

The gist of a seventh characteristic is that the seventh characteristic comprises the fifth characteristic or the sixth characteristic, and comprises an information source having the characteristic parameters or identification information associated with the characteristic parameters. Note that the information source comprising the characteristic parameters or the identification information associated with the characteristic parameters may be the above information source which holds the identification information associated with the correction value, or may be an information source different from the above information source.

The gist of an eighth characteristic is that the eighth characteristic comprises one of the first to seventh characteristics, wherein the reference amount of the aerosol is defined by a designed value of a amount of the aerosol that should be passed through the first branched flow path when the flow rate ratio coincides with the pre-designed value.

The gist of a ninth characteristic is that the ninth characteristic comprises the eighth characteristic, wherein the target amount of the aerosol is set to a value that is obtained by dividing the reference amount of the aerosol by the flow rate ratio.

The gist of a tenth characteristic is that the tenth characteristic comprises one of the first to seventh characteristics, wherein the reference amount of the aerosol is defined by a value that is obtained by dividing, by the pre-designed value of the flow rate ratio, a designed value of a amount of aerosol that should be passed through the first branched flow path when the flow rate ratio coincides with the pre-designed value.

The gist of an eleventh characteristic is that the eleventh characteristic comprises the tenth characteristic, wherein the target amount of the aerosol is set to a value that is obtained by dividing, by the flow rate ratio, a product of the reference amount of the aerosol and the pre-designed value.

The gist of a twelfth characteristic is that the twelfth characteristic comprises one of the first to eleventh characteristics, wherein the flavor inhaler comprises an atomizing unit comprising the atomizing section and a flavor unit comprising the flavor source, and the flavor unit is constructed to be attachable/detachable to/from the atomizing unit.

The gist of a thirteenth characteristic is that the thirteenth characteristic comprises the twelfth characteristic, wherein the information source is positioned in the flavor unit.

The gist of a fourteenth characteristic is that the fourteenth characteristic comprises the twelfth characteristic or the thirteenth characteristic, wherein the first branched flow path and the second branched flow path are positioned in the flavor unit.

The gist of a fifteenth characteristic is that the fifteenth characteristic comprises one of the twelfth to fourteenth characteristics, wherein calculation of the target amount of the aerosol is performed under a state that the flavor unit is being attached to the atomizing unit.

The gist of a sixteenth characteristic is that the sixteenth characteristic comprises the fifteenth characteristic, wherein calculation of the target amount of the aerosol is performed when a state that the flavor unit is attached to the atomizing unit is detected.

The gist of a seventeenth characteristic is that the seventeenth characteristic comprises one of the twelfth to fifteenth characteristics, wherein calculation of the target amount of the aerosol is performed when predetermined manipulation performed by a user is detected.

The gist of an eighteenth characteristic is that the eighteenth characteristic comprises the seventeenth characteristic, wherein the flavor inhaler comprises an inhaling sensor for detecting inhaling action performed by a user, and calculation of the target amount of the aerosol is performed when the inhaling action is detected by the inhaling sensor for the first time.

The gist of a nineteenth characteristic is that the nineteenth characteristic comprises one of the twelfth to eighteenth characteristics, wherein the control section reads the correction value via the information source, under a state that the flavor unit is being attached to the atomizing unit.

The gist of a twentieth characteristic is that the twentieth characteristic comprises one of the twelfth to eighteenth characteristics, wherein the control section reads the correction value via the information source, under a state that the flavor unit is not being attached to the atomizing unit.

The gist of a twenty-first characteristic is that the twenty-first characteristic comprises one of the first to twentieth characteristics, wherein, in the case that an accumulated value of amounts of the aerosol generated in the atomizing section or an accumulated value of amounts of the aerosol passed through the first branched flow path exceeds a first threshold value, the amount of the aerosol to be generated in the atomizing section is increased.

The gist of a twenty-second characteristic is that the twenty-second characteristic comprises one of the first to twenty-first characteristics, wherein, in the case that an accumulated value of amounts of the aerosol generated in the atomizing section or an accumulated value of amounts of the aerosol passed through the first branched flow path exceeds a second threshold value, supply of electric power to the atomizing section is cut off.

The gist of a twenty-third characteristic is that the twenty-third characteristic comprises one of the first to twenty-second characteristics, wherein the flavor inhaler comprises a battery unit comprising a battery.

The gist of a twenty-fourth characteristic is that the twenty-fourth characteristic comprises the twenty-third characteristic, wherein the battery unit is constructed to be attachable/detachable to/from the atomizing unit comprising the atomizing section.

The gist of a twenty-fifth characteristic is that the twenty-fifth characteristic comprises the twenty-third characteristic or the twenty-fourth characteristic, wherein the control section is positioned in the battery unit.

The gist of a twenty-sixth characteristic is that a cartridge comprises: an atomizing section for generating aerosol from an aerosol source; a flavor source positioned downstream the atomizing section; a mouthpiece section positioned downstream the flavor source; an aerosol flow path leading from the atomizing section to the mouthpiece section; and an information source for holding identification information associated with a correction value used for correcting a reference amount of the aerosol that is a amount of the aerosol to be generated in the atomizing section and is designed in advance; wherein the aerosol flow path is divided, in a part between the atomizing section and the flavor source, into a first branched flow path passing through the flavor source and a second branched flow path different from the first branched flow path; and the correction value is a value relating to a flow rate ratio of a flow rate in the second branched flow path to a predetermined flow rate at the time when the mouthpiece section is sucked at the predetermined flow rate.

The gist of a twenty-third characteristic is that a flavor unit, which is attachable/detachable to/from an atomizing unit comprising an atomizing section for generating aerosol, comprises: a flavor source; a mouthpiece section positioned downstream the flavor source; an aerosol flow path which is constructed to be able to communicate with the atomizing section in the atomizing unit and leads to the mouthpiece section; and an information source for holding identification information associated with a correction value used for correcting a reference amount of aerosol that is a amount of the aerosol to be generated in the atomizing section and is designed in advance; wherein the aerosol flow path is divided, in a part between the atomizing section and the flavor source, into a first branched flow path passing through the flavor source and a second branched flow path different from the first branched flow path; and the correction value is a value relating to a flow rate ratio of a flow rate in the second branched flow path to a predetermined flow rate at the time when the mouthpiece section is sucked at the predetermined flow rate.

BRIEF DESCRIPTION OF DRAWINGS

FIG. 4 is a flow chart showing correction of a reference amount of aerosol.

FIG. 7 is a flow chart showing an example of a method for controlling an atomizing section.

DESCRIPTION OF EMBODIMENTS

In the following description, embodiments of the present invention will be explained. In this regard, in the following descriptions of the figures, the same or similar symbols are assigned to the same or similar parts. Note that the figures are drawn in a schematic manner, thus, ratios between respective sizes of components may be different from those of actual components.

Thus, specific sizes and so on should be determined by taking the following description into consideration. Further, it is a matter of course that relationship between sizes and ratios between sizes of some parts drawn in one figure may be different from those in another figure.

Summary of Disclosure

A flavor inhaler, which relates to a summary of the disclosure, comprises: an atomizing section for generating aerosol from an aerosol source; a flavor source positioned downstream the atomizing section; a mouthpiece section positioned downstream the flavor source; a control section for controlling the atomizing section; an aerosol flow path leading from the atomizing section to the mouthpiece section; and an information source for holding identification information associated with a correction value used for correcting a reference amount of the aerosol that is a amount of the aerosol to be generated in the atomizing section and is designed in advance. The aerosol flow path is divided, in a part between the atomizing section and the flavor source, into a first branched flow path passing through the flavor source and a second branched flow path different from the first branched flow path. The correction value is a value relating to a flow rate ratio of a flow rate in the first branched flow path to a predetermined flow rate at the time when the mouthpiece section is sucked at the predetermined flow rate. The control section controls the atomizing section based on a target amount of the aerosol that is calculated based on the reference amount of the aerosol and the correction value.

In the above flavor inhaler, the control section can change, based on a ratio between a flow rate of the aerosol in the first branched flow path and a flow rate of the aerosol in the second branched flow path, a target amount of the aerosol that should be generated in the atomizing section. Thus, the control section can adjust, based on the above flow rate ratio, the amount of the aerosol passing through the first branched flow path.

First Embodiment

Flavor Inhaler

Figure 1:
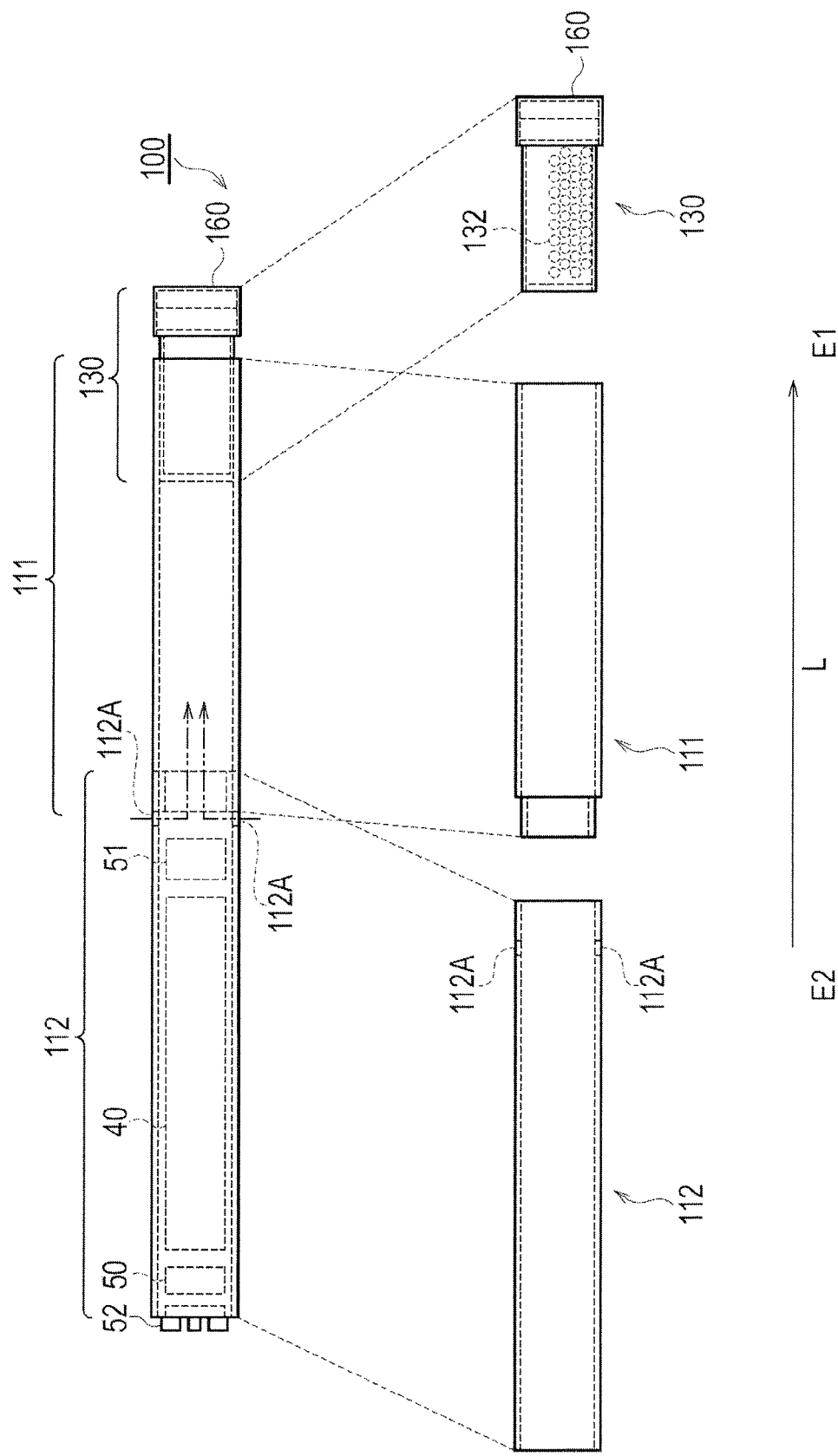
FIG. 1 is a figure showing a schematic construction of a flavor inhaler according to a first embodiment.
Figure 2:
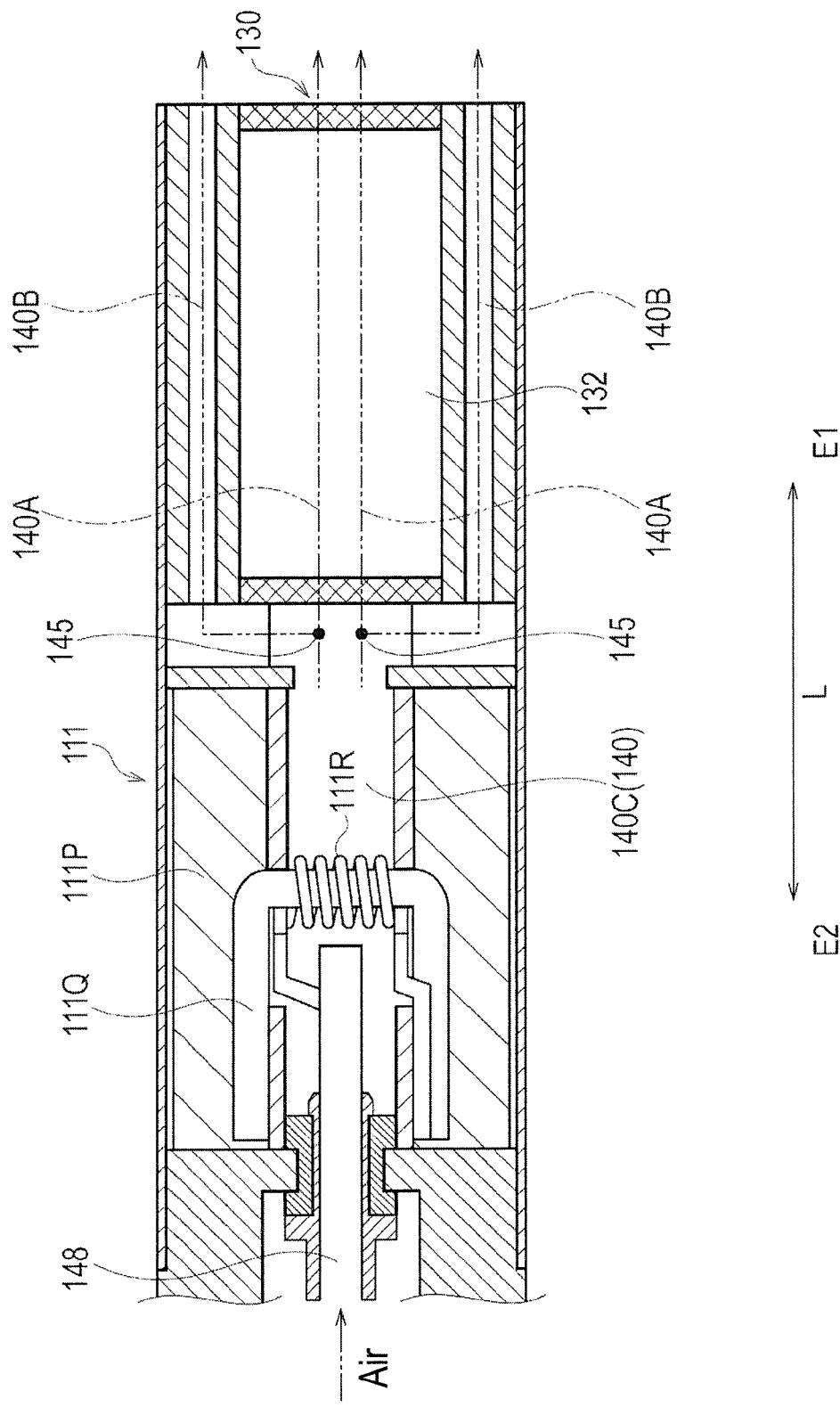
FIG. 2 is a figure showing constructions of an atomizing unit and a flavor unit.

In the following description, a flavor inhaler according to a first embodiment will be explained. FIG. 1 is a figure showing a flavor inhaler 100 according to the first embodiment. FIG. 2 is a figure showing an atomizing unit which is a component of the flavor inhaler 100.

The flavor inhaler 100 is a device which is used when inhaling an inhaling component (a flavor component) without a burning process. The flavor inhaler 100 may have a shape that extends in a predetermined direction L that is a direction from a non-mouthpiece end E2 to a mouthpiece end E1.

The flavor inhaler 100 comprises an atomizing unit 111, a battery unit 112, and a flavor unit 130. The atomizing unit 111 may be constructed to be attachable/detachable to/from the battery unit 112. The flavor unit 130 may be constructed to be attachable/detachable to/from the atomizing unit 111.

Instead of the above mode, the atomizing unit 111 and the battery unit 112 may be constructed in such a manner that they are integrated into a single unit, and the flavor unit 130 may be constructed to be attachable/detachable to/from the atomizing unit 111. Also, the flavor unit 130 and the atomizing unit 111 may be constructed in such a manner that they are integrated into a cartridge, and the cartridge may be constructed to be attachable/detachable to/from the battery unit 112.

The atomizing unit 111 comprises at least an atomizing section 111R. The atomizing section 111R generates aerosol from an aerosol source which will be explained later. In this embodiment, the atomizing unit 111 further comprises a reservoir 111P and a wick 111Q.

The reservoir 111P holds an aerosol source. The aerosol source may be a liquid such as glycerin or propylene glycol, for example. Note that the aerosol source may comprise a flavor source which includes a nicotine component or the like, or may not comprise a flavor source which includes a nicotine component or the like. The aerosol source may comprise a flavor source which includes a component other than a nicotine component, or may not comprise a flavor source which includes a component other than a nicotine component.

The reservoir 111P is constructed by use of fibrous or porous material. In such a case, the reservoir 111P can hold the aerosol source, which is in the form of fluid, by spaces between fibers or in pores in the porous material. Instead of the above construction, the reservoir 111P may be constructed by use of a tank for holding a liquid. The reservoir 111P may comprise a construction for allowing replenishment of the aerosol source, or a construction for allowing replacement of the reservoir itself when the aerosol source is exhausted.

The wick 111Q sucks the aerosol source held in the reservoir 111P. A part of the wick 111Q extends to the inside of the reservoir 111P and is in contact with the aerosol source. Another part of the wick 111Q extends toward the atomizing section 111R. The aerosol source is sent from the reservoir 111P to the atomizing section 111R by capillary effect in the wick 111Q. For example, the wick 111Q comprises glass fibers.

The atomizing section 111R atomizes the aerosol source sucked by the wick 111Q. For example, the atomizing section 111R comprises a resistance heating element which is positioned to be close to or in contact with the wick 111Q. The resistance heating element atomizes the aerosol source held by the wick 111Q. The resistance heating element comprises, for example, a resistance heating element wound, with a predetermined pitch, around the wick 111Q, for example, a heating wire. Instead of the above embodiment, the atomizing section 111R may comprise an ultrasonic-type atomizer which atomizes the aerosol source by ultrasonic vibration.

Instead of the above embodiment, the reservoir 111P and the wick 111Q may be arranged in the battery unit 112. In such a case, it may be constructed in such a manner that the atomizing section 111R is positioned to be close to or in contact with the wick 111Q when the atomizing unit 111 is attached to the battery unit 112.

Further, the atomizing unit 111 may comprise an information source 111M which stores characteristic information of the atomizing section 111R. The information source 111M comprises a memory, for example. In such a case, the control section 51, which will be explained later, can obtain the characteristic information of the atomizing section 111R from the memory. Regarding the characteristic information, an example thereof will be explained later.

The battery unit 112 comprises at least a battery 40 for storing electric power. The battery unit may comprise the control section 51. The control section 51 controls the atomizing section 111R in an electric manner. Specifically, the control section 51 controls electric energy supplied from the battery 40 to the atomizing section 111R. The control section 51 is an electronic circuit module constructed as a microprocessor or a microcomputer, and is programmed to control operation of the flavor inhaler 100 in accordance with computer-executable instructions stored in the memory. The memory comprises an information storing medium such as a ROM, a RAM, a flash memory, or the like. The memory may store, in addition to the computer-executable instructions, setting data which are necessary for controlling the flavor inhaler 100.

The flavor unit 130 comprises at least a flavor source 132. The flavor source 132 is positioned downstream the atomizing section 111R, and adds flavor to the aerosol generated by the atomizing section 111R. The flavor source 132 may comprise, for example, a source which originates from tobacco, such as shredded tobacco, a product which is made by processing raw material comprising tobacco to have a granular form, a sheet form, or a powder form, or the like, or a source which does not originate from tobacco, such as a product made by use of a plant other than tobacco (for example, mint, a herb, and so on). For example, the flavor source 132 comprises a nicotine component. The flavor source 132 may comprise a flavor component such as menthol or the like. For example, the flavor inhaler 100 may be constructed in such a manner that the flavor source 132 holds flavor material which originates from tobacco and the reservoir comprises flavor material which does not originate from tobacco.

The flavor inhaler 100 may comprise a mouthpiece section 160 which is constructed to be attachable/detachable to/from a part at an mouthpiece-end side of the flavor unit 130. The mouthpiece section 160 is a part which is held in a user's mouth during inhaling action. Note that the mouthpiece section 160 may be constructed in such a manner that it is integrated with the end part at the mouthpiece-end side of the flavor unit 130.

The flavor inhaler 100 comprises an aerosol flow path 140 and an air flow path 148. The air flow path 148 can guide air from a vent 112A to the inside of the flavor inhaler 100. The air flow path 148 leads from the vent 112A to atomizing section 111R.

The aerosol flow path 140 communicates with the air flow path 148, and is a flow path leading from the atomizing section 111R to the mouthpiece section. The aerosol flow path 140 guides a fluid, which comprises a mixture of the air taken into the air flow path 148 and the aerosol generated in the atomizing section 111R, to the mouthpiece section.

The aerosol flow path 140 comprises a shared flow path 140C, a first branched flow path 140A, and a second branched flow path 140B. Specifically, the aerosol flow path 140 is divided, in a part between the atomizing section 111R and the flavor source 132, into the first branched flow path 140A passing through the flavor source 132 and the second branched flow path 140B different from the first branched flow path 140A. A junction 145 of the first branched flow path 140A and the second branched flow path 140B is positioned between the atomizing section 111R and the flavor source 132.

The shared flow path 140C is a flow path leading from the atomizing section 111R to the junction 145. The first branched flow path 140A extends from the junction 145 to the mouthpiece section 160 via the flavor source 145. On the other hand, the second branched flow path 140B extends to the mouthpiece section 160 without passing through the flavor source 145.

The mixed fluid generated in the atomizing section 111R passes through the shared flow path 140C, and is separated at the junction 145 into parts for the first branched flow path 140A and the second branched flow path 140B. The aerosol flown into the first branched flow path 140A is provided with a flavor component supplied from the flavor source 132, and, thereafter, guided to the mouthpiece section 160. The aerosol flown into the second branched flow path 140B is guided to the mouthpiece section 160 without addition of the flavor component included in the flavor source 132. The aerosol from the first branched flow path 140A and the aerosol from the second branched flow path 140B is inhaled by a user via the mouthpiece section 160.

In this embodiment, the first branched flow path 110A and the second branched flow path 110B are joined at the mouthpiece section 160 downstream the flavor source 132. However, the above construction is not necessarily required. For example, there may be a construction wherein an end (the downstream-side end) of the second branched flow path 140B is joined, within the flavor source 132, to the first branched flow path 140A so that the aerosol flowing through the second branched flow path 140B passes through a part of the flavor source 132 (for example, a part at the downstream side of the flavor source 132). Further, although the first branched flow path 140A only is provided with the flavor source 132 in the flavor inhaler 100 shown as an example in FIG. 2, a flavor source different from the flavor source 132, for example, a flavor source which can add a flavor component, which is different from that included in the flavor source 106, to the aerosol may further be added to the second branched flow path 140B.

The flavor source 132 is not limited to that giving out flavor itself, and it may be material enhancing flavor when it is combined with a flavor component in the aerosol generated in the atomizing section 111R, for example, acid such as pyruvic acid, levulinic acid, etc., or the like.

The flavor inhaler 100 may comprise a sensor for detecting connection of the flavor unit 130 to the atomizing unit 111. For example, the flavor unit 130 may comprise a resistor which is electrically connected to an electric circuit in the atomizing unit 111 when the flavor unit 130 is connected to the atomizing unit 111. According to the above construction, an electric resistance value of a part of the electric circuit in the atomizing unit 111 changes when the flavor unit 130 is connected to the atomizing unit 111. The control section 51 can detect connection of the flavor unit 130 to the atomizing unit 111 by detecting change in the electric resistance value or change in current or voltage due to the change in the electric resistance value. Note that the sensor for detecting connection is not limited to that comprising the above construction, and the sensor may be that having an optional construction.

Further, the flavor inhaler 100 may comprise a sensor for detecting connection of the atomizing unit 111 to the battery unit 112. For example, the atomizing unit 111 may comprise a resistor which is electrically connected to an electric circuit in the battery unit 112 when the atomizing unit 111 is connected to the battery unit 112. According to the above construction, an electric resistance value of a part of the electric circuit in the battery unit 112 changes when the atomizing unit 111 is connected to the battery unit 112. The control section 51 can detect connection of the atomizing unit 111 to the battery unit 112 by detecting change in the electric resistance value or change in current or voltage due to the change in the electric resistance value. Note that the resistor which is installed in the atomizing unit 111 and used for detecting connection may be the atomizing section 111R itself. Further, the sensor for detecting connection is not limited to that comprising the above construction, and the sensor may be that having an optional construction.

The flavor inhaler 100 may comprise a contact sensor 52. The contact sensor 52 may be positioned in an end part at the non-mouthpiece side E2 of the flavor inhaler 100. The contact sensor 52 can detect a state that the contact sensor 52 is touched by a user. For example, the contact sensor has a pair of electrodes which are spaced apart from each other. When the pair of electrodes is brought into a conduction state by an external element such as a finger of a user, current flows between the electrodes in the pair. The contact sensor 52 can detect the conduction state of the pair of the electrodes by detecting the current. Thus, the contact sensor 52 can detect touching by a finger of a user. Such a contact sensor 52 may be used for judging whether a user is an authorized user. In such a case, for example, when the contact sensor 52 is touched in a predetermined touching manner by a user, the control section 51 may set the flavor inhaler 100 to be in a state wherein electric power can be supplied to the atomizing section 111R.

The flavor inhaler 100 may comprise a manipulation button which is manipulated by a user, or an inhaling sensor 50 for detecting inhaling action performed by a user. The inhaling sensor 50 may be a pressure sensor for detecting change in pressure in the air flow path 148 or the aerosol flow path 140. The control section 51 starts supply of electric power to the atomizing section 111R in response to pressing of the manipulation button or detection of inhaling action by the inhaling sensor 50. As a result thereof, the aerosol is generated in the atomizing section 111R.

As explained above, the fluid flowing through the aerosol flow path 140 is a fluid comprising a mixture of the aerosol generated in the atomizing section 111R and the air taken from the air flow path 148. It is supposed that a flow rate of the air and a flow rate of the aerosol flowing through the shared flow path 140C are Q and $A_f$, a flow rate of the air and a flow rate of the aerosol flowing through the first branched flow path 140A are $Q_1$ and $A_{f1}$, and a flow rate of the air and a flow rate of the aerosol flowing through the second branched flow path 140B are $Q_2$ and $A_{f2}$, respectively. In this regard, it is defined that $Q=Q_1+Q_2$ and $A_f=A_{f1}+A_{f2}$. Note that, in this specification, the "flow rate of air" means a volume flow rate (mL/sec), and the "flow rate of aerosol" means a mass flow rate (mg/sec). Further, it should be reminded in the following description that, in the case that the expression "flow rate," rather than the expression "flow rate of aerosol," is simply used, the "flow rate" means a flow rate of the air. Further, the flow rate of the air and the flow rate of the aerosol flowing through the shared flow path 140C are substantially equal to a total flow rate of the air and a total flow rate of the aerosol flowing through the aerosol flow path 140, respectively.

In this specification, it is defined that a flow rater ratio β is a ratio of a flow rate of the air flowing through the first branched flow path 110A to the total flow rate of the air flowing through the aerosol flow path 140 (i.e., $\beta=Q_1/Q$). In this regard, the flow rater ratio β is substantially equal to the ratio of the flow rate $A_{f1}$ of the aerosol flowing through the first branched flow path 140A to the total flow rate $A_f$ of the aerosol flowing through the aerosol flow path 140 (i.e., $\beta=Q_1/Q=A_{f1}/A_f$). Further, the flow rater ratio β is substantially equal to the ratio between a amount A of the aerosol generated in the atomizing section 111R and a amount $A_1$ of part of the aerosol generated in the atomizing section 111R and passed through the first branched flow path 140A, in predetermined time, for example, in the length of time required for performing a single puff action (i.e., $\beta=Q_1/Q=A_1/A$).

The flow rate ratio β is dependent on air-flow resistance of each of the first branched flow path 140A and the second branched flow path 140B. The air-flow resistance is dependent on the length and the cross-sectional area, the degree of bending, the shapes of a branching part and a junction part, and so on of the flow path.

Thus, the flow rate ratio β is a value specific to the flavor unit 130 or a value specific to a combination of the atomizing unit 111 and the flavor unit 130, and may change depending on each of atomizing units 111 and/or flavor units 130 attached to the battery unit 130. Specifically, in the case that a junction 145 and a first branched flow path 140A and a second branched flow path 140B downstream the junction 145 are positioned in each flavor unit 130, the flow rate ratio β changes depending on each of flavor units 130.

For example, each of atomizing units 111 and/or each of flavor units 130, which respectively have values of different flow rate ratios β positively, may be constructed to be attachable/detachable to/from the battery unit 112. In such a case, the flow rate ratio β may be changed positively according to the type and/or the amount of the flavor source 132 included in each flavor unit 130, for example.

In another example, flow rate ratios β relating to atomizing units 111 and/or flavor units 130 may vary from one unit to another, since there may be variation between lots thereof due to manufacturing errors even if an effort to manufacture the atomizing units 111 and/or the flavor units 130 as designed is made. Thus, even in the case that products (atomizing units 111 and/or flavor units 130) which are designed to be similar to each other are used, flow rate ratios may vary from one product to another.

In the case that the flow rate ratio β is changed, the amount of aerosol passing through the first branched flow path 140A, thus, the flavor source 132, is changed, even if the amount of aerosol generated in the atomizing section 111R is maintained to be constant.

It is preferable that the first branched flow path 140A, the second branched flow path 140B, and the junction 145 be positioned in the flavor unit 130. In such a case, the flow rate ratio β is determined for each flavor unit 130, and is not substantially dependent on an atomizing unit 111. Instead of the above construction, part of the first branched flow path 140A and the second branched flow path 140B and the junction 145 may be positioned in the atomizing unit 111. In such a case, the flow rate ratio β is determined with respect to a combination of a flavor unit 130 and an atomizing unit 111.

In this embodiment, the control section 51 controls the atomizing section 111R, based on the flow rate ratio β, for changing the amount of the aerosol to be generated in the atomizing section 111R. For the above purpose, the flavor inhaler 100 comprises an information source 134M for holding identification information associated with correction values. Specifically, a correction value is a value used for correcting a reference amount $A_R$ of aerosol that is the amount of aerosol to be generated in the atomizing section 111R and is designed in advance. Note that, as will be explained later, the above-explained information source 111M is that for storing identification information different from that stored in the information source 134M.

For example, the information source 134M may be a memory which stores identification information associated with a correction value that is used for correcting the reference amount $A_R$ of aerosol. The information source 134M may be positioned in the flavor unit 130. In the case that the atomizing unit 111 and the flavor unit 130 are integrated into a cartridge, the information source 134M may be positioned in the cartridge, thus, in the flavor unit 130 or the atomizing unit 111. In such a case, the information sources 111M and 134M may be constructed by use of the same memory.

The correction value is a value relating to a flow rate ratio $\beta$ of a flow rate $Q_1$ of the first branched flow path 140A to a predetermined flow rate $Q_A$ when inhaling action with the predetermined flow rate is performed at the mouthpiece section 160. Specifically, the correction value may be the value of the flow rate ratio $\beta$ itself. Note that it is considered that the predetermined flow rate $Q_A$ in the mouthpiece section 160 is substantially equal to the flow rate Q in the shared flow path 140C.

Instead of the above construction, the correction value may be defined as a parameter that can be converted to the flow rate ratio $\beta$. Examples of such parameters are a ratio of the flow rate $Q_2$ of the second branched flow path 140B to the predetermined flow rate $Q_A$, a ratio between the flow rate $Q_1$ of the first branched flow path 140A and the flow rate $Q_2$ of the second branched flow path 140B, and so on. The correction values are not limited to the above examples, and may be one or more optional parameters that can be used for calculating the flow rate ratio $\beta$.

Note that the values of the flow rate $Q_1$ of the first branched flow path 140A and/or the flow rate $Q_2$ of the second branched flow path 140B to the predetermined flow rate $Q_A$ are determined by performing measurement in advance, i.e., by performing measurement when manufacturing the atomizing unit 111 and the flavor unit 130. For example, with respect to a manufactured flavor unit 130 or a manufactured cartridge comprising a flavor unit 130 and an atomizing unit 130 in each lot to which it belongs, inhaling operation at a predetermined flow rate $Q_A$ at a mouthpiece section 160 is performed. By actually measuring the flow rates $Q_1$ and $Q_2$ by the measurement, a value of the correction value can be determined. The correction value is stored in the information source 134M in advance.

Note that it is expected that the flavor units 130 or the cartridges, each of which comprising a flavor unit 130 and an atomizing unit 130, manufactured as members of a single production lot have the substantially same flow rate ratio $\beta$. Thus, it is not necessarily required to perform the above measurement for all products in a single production lot, and the correction value may be determined on the supposition that the same flow rate ratio $\beta$ can be obtained for all products in a single production lot.

Correction of the Amount of Aerosol

As shown in FIG. 4, the control section 51 obtains, at predetermined timing, the above correction value via the information source 134M (step S101). As a result thereof, the control section 51 can obtain a flow rate ratio $\beta$. The flow rate ratio $\beta$ is used for correcting the amount of aerosol to be generated in the atomizing section 111R.

A reference amount $A_R$ of aerosol is a amount of aerosol to be generated in the atomizing section 111R, and is defined by a pre-designed amount. More specifically, in the first embodiment, the reference amount $A_R$ of aerosol is defined by a designed value of a amount of aerosol that should be passed through the first branched flow path 140A when the flow rate ratio is equal to a pre-designed reference value. Specifically, the reference amount $A_R$ of aerosol is defined by an initial set value of the amount of aerosol that should be passed through the first branched flow path 140A. Thus, the reference amount $A_R$ of aerosol is not dependent on an actual flow rate ratio $\beta$. The reference amount $A_R$ of aerosol may be stored in a memory in the control section 51 or the information source 134M in advance.

The reference amount $A_R$ of aerosol may have a constant value regardless of the type and/or the amount of the flavor source 132. In such a case, the reference amount $A_R$ of aerosol may be stored in a memory in the control section 51. Instead of the above construction, the reference amount $A_R$ of aerosol may have a value that is different from one flavor unit 130 to another, according to the type and/or the amount of the flavor source 132. In such a case, the reference amount $A_R$ of aerosol may be stored in the information source 134M.

The control section 51 determines, at predetermined timing, a target amount $A_T$ of aerosol based on the reference amount $A_R$ of aerosol and the flow rate ratio $\beta$ (step S102). That is, the control section 51 changes, based on the flow rate ratio $\beta$, the target amount $A_T$ of aerosol that should be atomized in the atomizing section 111R.

Thereafter, in response to pressing of the manipulation button by a user or detection of inhaling action by the inhaling sensor 50, the control section 51 controls the atomizing section 111R in such a manner that the target amount $A_T$ of aerosol is generated in the atomizing section 111R. Note that, in the case that the amount of aerosol generated in the atomizing section 111R can be adjusted based on electric power supplied to the atomizing section 111R, the control section 51 may determine target electric energy $E_T$ supplied to the atomizing section 111R, so as to make the atomizing section 111R to generate the target amount $A_T$ of aerosol that is determined as explained above. Details of the target electric energy $E_T$ will be explained later.

According to the above mode, in the case that flavor units 130 or cartridges, each of which comprising a flavor unit 130 and an atomizing unit 111, having different flow rate ratios $\beta$ are positively used, the most suitable target amount $A_T$ of aerosol is determined based on the type and/or the amount of a flavor source 132 included in a flavor unit 130. Since the control section 51 controls the atomizing section 111R in such a manner that the target amount $A_T$ of aerosol is generated in the atomizing section 111R, an actual flow rate of the aerosol that is to be passed through the flavor source 132 can be adjusted to a most suitable value based on the type and/or the amount of the flavor source 132 included in the flavor unit 130.

As a tangible example, in the case that the flow rate ratio $\beta$ is larger than a pre-designed value, the target amount $A_T$ of aerosol is set to be smaller than a target amount of the aerosol in the case that the flow rate ratio $\beta$ coincides with the pre-designed value; and, in the case that the flow rate ratio $\beta$ is smaller than the pre-designed value, the target amount $A_T$ of aerosol is set to be larger than the target amount of the aerosol in the case that the flow rate ratio $\beta$ coincides with the pre-designed value. In such a case, the target amount $A_T$ of aerosol becomes smaller as the flow rate of the first branched flow path 140A becomes larger, and the target amount $A_T$ of aerosol becomes larger as the flow rate of the first branched flow path 140A becomes smaller. Thus, even if change in the flow rate ratio β has occurred, the amount of aerosol flowing through the first branched flow path 140A during a single puff action can be made to be uniform to some extent.

In another tangible example, the control section 51 may determine the target amount $A_T$ of aerosol based on the reference amount $A_R$ of aerosol and the flow rate ratio β in such a manner that the target amount $A_T$ of aerosol satisfies formula "$A_T=A_R/β$." That is, the target amount $A_T$ of aerosol is set to a value obtained by dividing the reference amount $A_R$ of aerosol by the flow rate ratio β. In such a case, the target amount $A_T$ of aerosol is determined to satisfy the condition that the amount of aerosol flowing through the first branched flow path 140A during a single puff action is made to be constant regardless of the flow rate ratio β. As a result thereof, even if any flavor unit 130 or any cartridge comprising a flavor unit 130 and an atomizing unit 110 is used, a user can inhale an approximately constant amount of flavor components in a single puff action. In this regard, in the flavor inhaler 100 according to the above mode, the control section 51 can make the amount of the aerosol flowing through the first branched flow path 140A to be uniform, by suppressing change in the flow rate ratios β due to variation between production lots. Thus, change in the amount of flavor components inhaled by a user, that occurs due to variation between production lots that is due to manufacturing errors, can be suppressed. Further, since change in the amount of flavor components, that occurs due to variation in the lots that occurs due to manufacturing errors, can be suppressed, a stable amount of aerosol can be sent to pass through the flavor source 132, even if the fabrication tolerance is set to be large.

Note that the amounts of flavor supplied to a user are not necessarily maintained to be a precisely equal value. For example, the control section 51 may control the atomizing section 111R for suppressing, to some extent, change in the amount of the aerosol passing through the first branched flow path 140A.

Timing for Obtaining a Correction Value

Timing that the control section 51 obtains a correction value, that is a value relating to a flow rate ratio β, is at least that before calculating a target amount $A_T$ of aerosol. In this embodiment, under the state that the flavor unit 130 is attached to the atomizing unit 111, or the state that the cartridge comprising the flavor unit 130 and the atomizing unit 111 is attached to the battery unit 112, the control section 51 can read a correction value via the information source 134M.

For example, when connection of the flavor unit 130 to the atomizing unit 111 attached to the battery unit 112 is detected, the control section 51 may obtain a correction value via the information source 134M. In another example, in the case that the atomizing unit 111 and the flavor unit 130 are integrated into a cartridge, the control section 51 may obtain a correction value via the information source 134M when connection of the cartridge to the battery unit 112 is detected.

In another example, under the state that the flavor unit 130 is connected to the atomizing unit 111 attached to the battery unit 112, or the state that the cartridge, which comprises a construction that the atomizing unit 111 and the flavor unit 130 are integrated into it, is attached to the battery unit 112, the control section 51 may obtain a correction value via the information source 134M, when a manipulation button for starting atomization is pressed by a user or when inhaling action is detected by the inhaling sensor 50. In such a case, the correction value may be obtained when the manipulation button for starting atomization is pressed by a user for the first time or when inhaling action is detected by the inhaling sensor 50 for the first time, after the flavor unit 130 is connected to the atomizing unit 111 attached to the battery unit 112, or after the cartridge, which comprises a construction that the atomizing unit 111 and the flavor unit 130 are integrated into it, is connected to the battery unit 112. In such a case, regarding the correction value obtaining process, a single number of time of execution of the process, after connection of the flavor unit 130 or the cartridge, is sufficient. However, it is also possible to construct the control section 51 to obtain a correction value via the information source 134M every time the manipulation button for starting atomization is pressed by a user or every time inhaling action is detected by the inhaling sensor 50.

Further, the control section 51 may be constructed in such a manner that it obtains a correction value via the information source 134M when the manipulation button for starting atomization is pressed in a predetermined pressing manner by a user or when inhaling action in a predetermined inhaling manner is detected by the inhaling sensor 50, under the state that the flavor unit 130 is connected to the atomizing unit 111 attached to the battery unit 112, or the state that the cartridge, which comprises a construction that the atomizing unit 111 and the flavor unit 130 are integrated into it, is attached to the battery unit 112.

Further, the control section 51 may be constructed in such a manner that it obtains a correction value via the information source 134M when conduction in a predetermined conducting manner is detected by the contact sensor 52, under the state that the flavor unit 130 is connected to the atomizing unit 111 attached to the battery unit 112, or the state that the cartridge, which comprises a construction that the atomizing unit 111 and the flavor unit 130 are integrated into it, is attached to the battery unit 112.

Timing for Calculating a Target Amount of Aerosol

Timing that the control section 51 calculates a target amount of aerosol is at least that after obtaining a correction value. In this embodiment, under the state that the flavor unit 130 is attached to the atomizing unit 111, or the state that the cartridge comprising the flavor unit 130 and the atomizing unit 111 is attached to the battery unit 112, the control section 51 can calculate a target amount of aerosol.

For example, when connection of the flavor unit 130 to the atomizing unit 111 attached to the battery unit 112 is detected, the control section 51 may obtain a correction value via the information source 134M and calculate, based thereon, a target amount of aerosol. In another example, in the case that the atomizing unit 111 and the flavor unit 130 are integrated into a cartridge, the control section 51 may obtain a correction value via the information source 134M and calculate, based thereon, a target amount of aerosol, when connection of the cartridge to the battery unit 112 is detected.

In another example, under the state that the flavor unit 130 is connected to the atomizing unit 111 attached to the battery unit 112, or the state that the cartridge, which comprises a construction that the atomizing unit 111 and the flavor unit 130 are integrated into it, is attached to the battery unit 112, the control section 51 may calculate a target amount of aerosol, when the manipulation button for starting atomization is pressed by a user or when inhaling action is detected by the inhaling sensor 50. In such a case, calculation of the target amount of aerosol may be performed when the manipulation button for starting atomization is pressed by a user for the first time or when inhaling action is detected by the inhaling sensor 50 for the first time, after the flavor unit 130 is connected to the atomizing unit 111 attached to the battery unit 112, or after the cartridge, which comprises a construction that the atomizing unit 111 and the flavor unit 130 are integrated into it, is connected to the battery unit 112. In such a case, regarding the calculation of the target amount of aerosol, a single number of time of calculation, after connection of the flavor unit 130 or the cartridge, is sufficient. However, it is also possible to construct the control section 51 to calculate a target amount of aerosol every time the manipulation button for starting atomization is pressed by a user or every time inhaling action is detected by the inhaling sensor 50.

Further, the control section 51 may be constructed in such a manner that it calculates a target amount of aerosol when the manipulation button for starting atomization is pressed in a predetermined pressing manner by a user or when inhaling action in a predetermined inhaling manner is detected by the inhaling sensor 50, under the state that the flavor unit 130 is connected to the atomizing unit 111 attached to the battery unit 112, or the state that the cartridge, which comprises a construction that the atomizing unit 111 and the flavor unit 130 are integrated into it, is attached to the battery unit 112.

Further, the control section 51 may be constructed in such a manner that it calculates a target amount of aerosol when conduction in a predetermined conducting manner is detected by the contact sensor 52, under the state that the flavor unit 130 is connected to the atomizing unit 111 attached to the battery unit 112, or the state that the cartridge, which comprises a construction that the atomizing unit 111 and the flavor unit 130 are integrated into it, is attached to the battery unit 112.

Control of Supply of Electric Power to the Atomizing Section

As explained above, the control section 51 controls the atomizing section 111R in such a manner that the amount of the aerosol generated in the atomizing section 111R becomes the same as a target amount $A_T$ of the aerosol. The control section 51 can control the amount of the aerosol to be generated in the atomizing section 111R by changing electric energy supplied from the battery 40 to the atomizing section 111R. Relationship between electric energy supplied to the atomizing section 111R and amounts of aerosol generated by use of the electric energy may be stored in the information source 111M in advance, for example. The control section 51 can obtain, by referring to the information source 111M and based on the target amount $A_T$ of the aerosol, electric energy that should be supplied to the atomizing section 111R.

Instead of the above construction, electric power to be supplied to the atomizing section 111R may be calculated based on a relational expression by which relationship between the amount of the aerosol generated in the atomizing section 111R and electric energy supplied to the atomizing section 111R is derived. The above matter will be explained in the following description.

Figure 5:
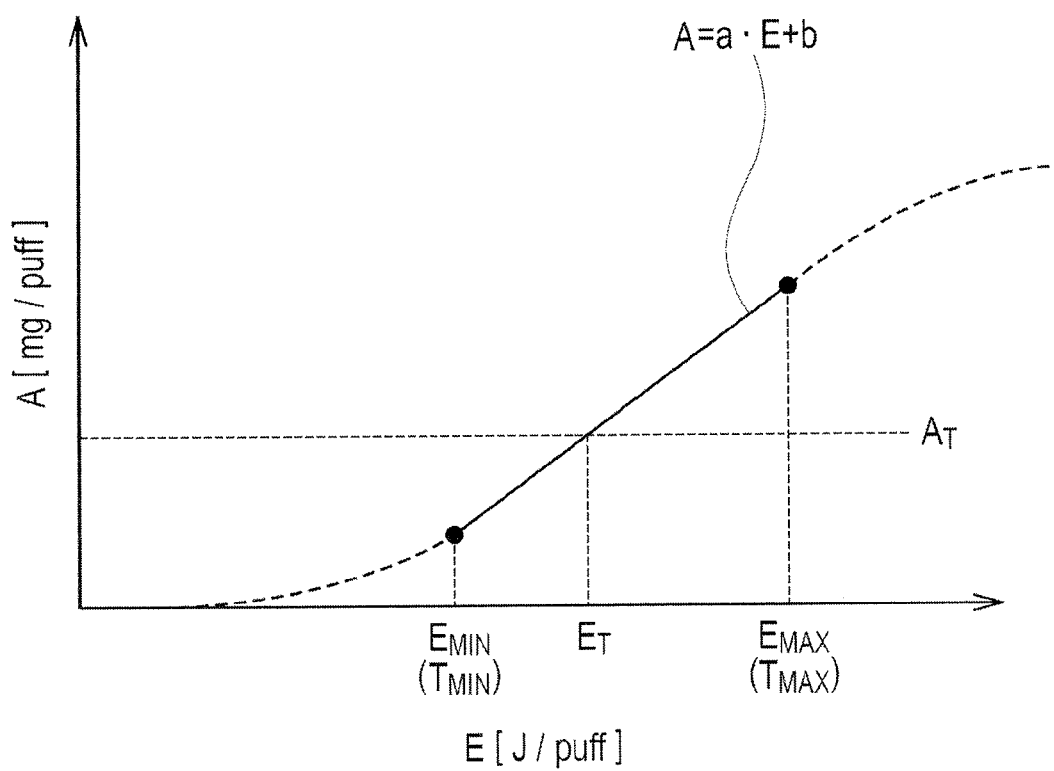
FIG. 5 is a figure showing relationship between electric energy supplied to an atomizing section and amounts of aerosol generated in the atomizing section.

Regarding the case that the atomizing section 111R comprises a resistance heating element, the inventors et al. found as a result of diligent study that there is linear relationship between electric energy E supplied to the atomizing section 111R and amounts A of aerosol generated in the atomizing section 111R, and that such linear relationship is different from one atomizing section 111R to another (refer to FIG. 5). In FIG. 5, the vertical axis represents the amounts A of aerosol (mg/puff), and the horizontal axis represents electric energy E (J/puff). The amounts A of aerosol generated in the atomizing section 111R and the electric energy E supplied to the atomizing section 111R have linear relationship in a range from a lower-limit electric energy $E_{MIN}$ to an upper-limit electric energy $E_{MAX}$.

The linear relationship is represented by "A=a*E+b." In the above expression, "A" represents the amount of aerosol generated in the atomizing section per a single puff action. "E" represents the electric energy supplied to the atomizing section 111R per a single puff action. "a" and "b" represent characteristic parameters of the atomizing unit 111. The characteristic parameters of the atomizing unit 111 depend on the composition of the wick 111Q, the composition of the atomizing section 111R, the composition of the aerosol source, the structure of the atomizing unit 111 (the wick 111Q and the resistance heating element 111R), and so on. Thus, the characteristic parameters "a" and "b" are different from one atomizing unit 111 to another. Also, regarding the parameters $E_{MIN}$ and $E_{MAX}$, since they are different from one atomizing unit 111 to another, it is possible to consider that they are characteristic parameters of the atomizing unit 111.

It is preferable that the characteristic parameters "a" and "b" be stored, in advance, in the information source 111M positioned in the atomizing unit 111. In such a case, the control section 51 can determine the target amount $A_T$ of the aerosol by obtaining the characteristic parameters "a" and "b" from the information source 111M and the flow rate ratio $\beta$ from the information source 134M.

The control section 51 can calculate, based on a relational expression "A=a*E+b," a target amount $E_T$ of electric energy that is required for generating the target amount $A_T$ of the aerosol. That is, in the case that values of the characteristic parameters "a" and "b" have been known, the control section 51 can calculate the target amount $E_T$ of electric energy by use of the target amount $A_T$ of the aerosol in such a manner that a relational expression "$E_T=(A_T-b)/a$" is satisfied. Regarding the target amount $A_T$ of the aerosol, explanation thereof is the same as the above explanation.

Thus, in the case that the target amount $A_T$ of the aerosol is determined based on the reference amount $A_R$ of aerosol and the flow rate ratio $\beta$ and by use of a relational expression "$A_T=A_R/\beta$," the control section 51 can calculate the target amount $E_T$ of electric energy by use of the target amount $A_T$ of the aerosol in such a manner that a relational expression "$E_T=(A_R/\beta-b)/a$" is satisfied. Note that, in the case that the value of |b| is sufficiently smaller than the value of $|A_R/\beta|$, approximation of b=0 in the above relational expression may be possible.

Note that the information source 111M positioned in the atomizing unit 111 may store values of the parameters "a" and "b." Then, the control section 51 can obtain the values of the parameters "a" and "b" via the information source 111M.

Also, the information source 111M may further store values of the parameters $E_{MIN}$ and $E_{MAX}$. In this regard, in the case that the atomizing section 111R comprises a resistance heating element, the electric energy E is affected by a voltage $V_S$ applied to the atomizing section 111R and the length of time T of application of the voltage $V_S$. Thus, $E_{MIN}$ and $E_{MAX}$ may be specified by use of the voltage $V_S$ and application time $T_{MIN}$ and $T_{MAX}$. That is, the above-explained information source 111M may store the voltage $V_S$ and the application time $T_{MIN}$ and $T_{MAX}$, instead of the parameters $E_{MIN}$ and $E_{MAX}$. Note that the voltage $V_S$ is a parameter used for replacing $E_{MIN}$ and $E_{MAX}$ with $T_{MIN}$ and $T_{MAX}$, and may be a constant value. In the case that the voltage $V_S$ is a constant value, the voltage $V_S$ may not be stored in the information source 111M. In the embodiment, the voltage $V_S$ corresponds to a reference voltage value $V_C$ that will be explained later, and the information source 111M stores the parameters $T_{MIN}$ and $T_{MAX}$.

The control section 51 may control the atomizing section 111R in such a manner that the electric energy E(T) per a single puff action does not exceeds $E_{MAX}$ ($T_{MAX}$). Specifically, for example, in the case that the electric energy E (T) has reached $E_{MAX}$ ($T_{MAX}$), the control section 51 terminates supply of electric power to the resistance heating element 111R.

In the case that the electric energy supplied to the atomizing section 111R is represented by E, the value of the output voltage of the battery 40 is represented by V, the length of time that the voltage is applied to the atomizing section is represented by T, and the value of the electric resistance of the atomizing section (the resistance heating element) 111R is represented by R, a relational expression "$E=(V^2/R)*T$" is satisfied. Thus, the control section 51 can calculate, from the target amount $E_T$ of electric energy required for generating the target amount $A_T$ of aerosol and by use of a relational expression "$E_T=(V^2/R)*T$," the value V of the output voltage of the battery 40 and the length of time T that the voltage is applied to the atomizing section. Note that, as explained above, the target amount $E_T$ of electric energy can be determined based on the target amount $A_T$ of aerosol. The output voltage value that is required for generating the target amount $A_T$ of aerosol and the length of time that the output voltage having the above value should be applied to the atomizing section can be calculated by use of the relational expression "$E_T=(V^2/R)*T$."

Note that V and T are values that are detectable by the control section 51, and R is a value that is obtainable by the control section 51 by reading it from the information source 111M. That is, it is preferable that the information source 111M store the electric resistance value R of the atomizing section (the resistance heating element) 111R. Note that R may be estimated by the control section 51.

Thus, the control section 51 performs control in such a manner that electric power is supplied to the atomizing section 111R according to the output voltage value and the application time that are calculated as explained above. As a result thereof, the above-explained target amount $A_T$ of aerosol can be generated in the atomizing section 111R.

Figure 6:
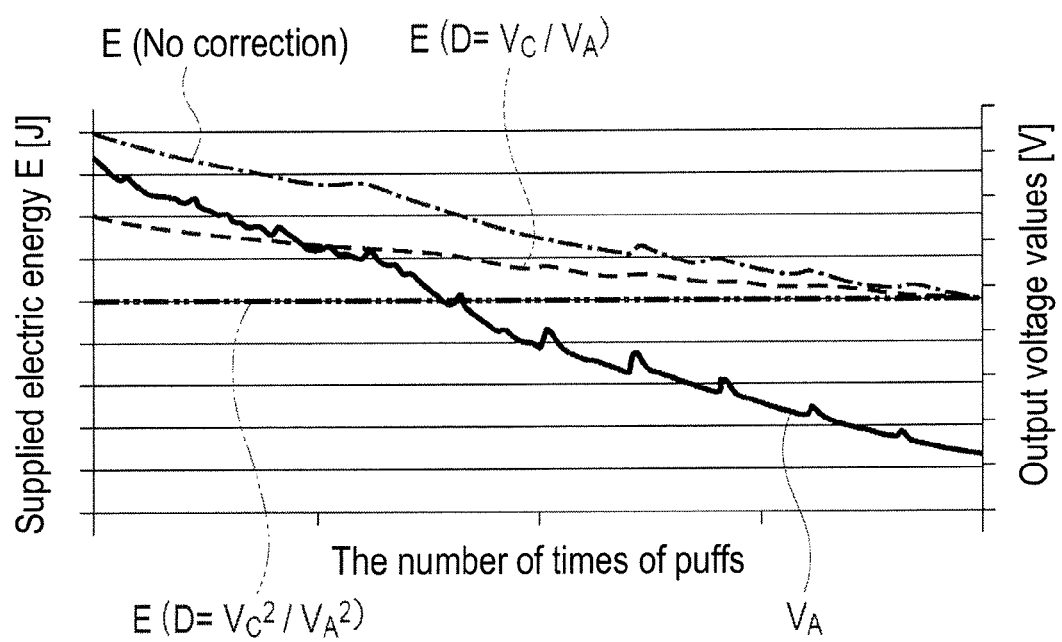
FIG. 6 is a figure showing correction for dealing with voltage drop in a battery.

In the case that a user performs plural puff actions, the control section 51 may supply electric power, that is determined based on the same voltage value and the same application time, to the atomizing section 111R during each puff action in the plural puff actions, for example. Instead, in the case that it is assumed that voltage drop of the battery 40 relating to increase in the number of times of puff actions (the number of times of puffs) occurs as shown in FIG. 6, it is preferable that the control section 51 correct the output voltage value of the battery 40 and the application time according to the number of times of puffs, for suppressing reduction, that is due to voltage drop of the battery 40, of electric power supplied to the atomizing section. Regarding the above case, if the electric energy supplied to the atomizing section 111R is represented by E, the value of the output voltage of the battery 40 is represented by V, the length of time that the voltage is applied to the atomizing section is represented by T, and the value of the electric resistance of the atomizing section (the resistance heating element) 111R is represented by R, a relational expression "$E=D*(V^2/R)*T$" is generally satisfied (refer to FIG. 6). In the above expression, D is a correction term relating to the voltage drop.

Specifically, the correction term D is calculated based on the output voltage value $V_A$ of the battery 40 and the reference voltage value $V_C$ of the battery. The reference voltage value $V_C$ is a value that is predetermined in accordance with the type of the battery 40 and so on, and is higher than at least the cut-off voltage of the battery 40. In the case that the battery 40 is a lithium-ion battery, the reference voltage value $V_C$ may be set to 3.2V.

In detail, as shown in FIG. 6, the output voltage value $V_A$ of the battery 40 decreases as the number of times of puffs increases. Thus, in the case that correction by use of the correction term D is not performed, the electric energy E supplied to the atomizing section decreases as the number of times of puffs increases (refer to the dot-dash-line in FIG. 6). As a result, the amount A of the aerosol generated per a single puff increases as the number of times of puffs increases.

For solving the above problem, the control section 51 sets the correction term D by use of a formula "$D=V_C/V_A$." By introducing such a correction term, reduction of the electric energy E supplied to the atomizing section 111R, when the output voltage value $V_A$ of the battery is decreased, can be mitigated. Preferably, the control section 51 sets the correction term D by use of a formula "$D=V_C^2/V_A^2$." By introducing such a correction term, reduction of the electric energy E supplied to the atomizing section 111R, when the output voltage value $V_A$ of the battery is decreased, can be further mitigated.

In view of the above-explained voltage drop of the battery 40, the control section 51 can calculate the value V of voltage that should be applied to the atomizing section 111R and the application time T, from the target amount $E_T$ of the electric energy required for generating the target amount $A_T$ of the aerosol and based on a relational expression "$E_T=D*(V^2/R)*T$." Note that the target amount $E_T$ of the electric energy can be determined based on the target amount $A_T$ of the aerosol as explained above. By determining the voltage value V and the application time T based on the above relational expression and the target amount $E_T$ of the electric energy supplied to the atomizing section 111R, the amount of the aerosol generated per a single puff action can be equalized even in the case that voltage drop has occurred in the battery 40, while taking the target amount $A_T$ of the aerosol, i.e., the correction value relating to the flow rate ration β, into consideration.

In this regard, adjustment of the electric energy to be supplied to the atomizing section 111R is made by performing adjustment of the absolute value of the voltage applied to the resistance heating element 111R, or adjustment of the application time of the voltage applied to the resistance heating element 111R (i.e., the pulse width and the pulse interval), or a combination of the above two types of adjustment. Note that correction of the absolute value of the value of the voltage applied to the atomizing section 111R is realized by use of a DC/AC converter. The DC/AC converter may be a step-down converter, or may be a step-up converter.

Note that the control section may also be able to estimate the amount of the aerosol generated in the atomizing section 111R, from the amount of electric energy suppled to the atomizing section 111R or from the applied voltage and the application time, and based on the relational expression "A=a*E+b" and the expression "E=(V²/R)*T" or "E=D*(V²/R)*T."

In this regard, the amount of the aerosol generated per a single puff action is substantially equal to the amount of the aerosol source consumed per a single puff action. Thus, the control section 51 may also be able to estimate the consumed amount of the aerosol source, from the amount of electric energy suppled to the atomizing section 111R or from the applied voltage and the application time, and based on the relational expression "A=a*E+b" and the expression "E=(V²/R)*T" or "E=D*(V²/R)*T."

Control of the Atomizing Section During Puff Action

FIG. 7 is a flow chart showing operation of the atomizing section that is performed when electric power is supplied to the atomizing section 111R, i.e., when puff action is performed. The control section 51 calculates an accumulated value of amounts of aerosol generated in the atomizing section 111R during puff action (step S702). As explained above, the amount of the generated aerosol can be estimated based on the amount of electric energy supplied to the atomizing section 51. That is, the amount of the aerosol generated in the atomizing section 111R per a single puff action can be estimated, for example, by use of the relational expression "A=a*E+b," specifically, "E=(V²/R)*T," more specifically, "E=D*(V²/R)*T."

The control section 51 observes, over time, the electric energy (=electric power*conduction time) supplied from the battery 40 to the atomizing section 111R, and successively adds the amounts of the generated aerosol that are estimated based on the electric energy. Thus, the control section 51 can obtain, in an estimate manner, the accumulated value of the amounts of the aerosol generated in the atomizing section 111R.

The control section 51 calculates an accumulated value of amounts of the aerosol passed through the first branched flow path 140A (step S704). The amount of the aerosol passed through the first branched flow path 110A can be calculated based on the estimated value of the amount of the aerosol generated in the atomizing section 111R and the flow rate ratio β. The control section 51 may calculate an accumulated value of amounts of the aerosol passed through the second branched flow path 140B in a manner similar to that explained above. Note that step S704 is optional, and it may be omitted.

The control section 51 judges whether the accumulated value of the amounts of the aerosol generated in the atomizing section 111R exceeds a first threshold value (step S706). If the accumulated value of the amounts of the aerosol exceeds the first threshold value, the process proceeds to step S708 that will be explained later, and, if not, the process returns to previous step S702.

In above step 704, in the case that an accumulated value of the amounts of the aerosol passed through the first branched flow path 140A is calculated, the control section 51 may be constructed in such a manner that it judges whether the accumulated value of the amounts of the aerosol passed through the first branched flow path 140A exceeds a predetermined threshold value that corresponds to the above first threshold value, instead of judging whether the accumulated value of the amounts of the aerosol generated in the atomizing section 111R exceeds the first threshold value.

The judgment in step S706 may be performed at any of timing 1) after a single puff action is completed, 2) during a predetermined time lag that is between a point in time when a puff action is detected by the inhaling sensor 50 and a point in time when atomizing of aerosol is started, or 3) during puff action (during a period of electric conduction to the atomizing section 111R), for example.

In step S708, the control section 51 changes the amount of aerosol generated in the atomizing section 51. Specifically, the control section 51 controls the atomizing section 111R in such a manner that the amount of aerosol passing through the first branched flow path 140A increases. Ability of the flavor source 132 to release flavor components may be degraded gradually due to flow of aerosol passing through it. For compensating for lowering of the amount of the flavor components released from the flavor source 132, the control section 51 performs control for increasing the amount of the aerosol passing through the first branched flow path 140A when the accumulated value of the aerosol passing through the first branched flow path 140A exceeds the predetermined first threshold value. In such a case, the first threshold value used in judgment performed in step S706 corresponds to an accumulated amount of aerosol that is sufficient for consuming a certain amount of the flavor components from the flavor source 132. As a result of control such as that explained above, the flavor inhaler 100 can suppress effect due to consumption of the flavor source 132, and equalize the amounts of flavor components supplied to a user for a long period.

In step S710, the control section 51 judges whether the accumulated value of the amounts of the aerosol generated in the atomizing section 111R exceeds a second threshold value. If the accumulated value of the amounts of the generated aerosol exceeds the second threshold value, the process proceeds to step S712, and, if not, the process returns to first step S702. The second threshold value is a value larger than the above first threshold value. In the case that an accumulated value of the amounts of the aerosol passed through the first branched flow path 140A is calculated in step S704, the control section 51 may be constructed in such a manner that it judges whether the accumulated value of the amounts of the aerosol passed through the first branched flow path 140A exceeds a predetermined threshold value that corresponds to the above second threshold value, instead of judging whether the accumulated value of the amounts of the aerosol generated in the atomizing section 111R exceeds the second threshold value.

In step S712, the control section 51 performs control to stop supply of electric power to the atomizing section 111R. As a result thereof, the flavor inhaler 100 can prevent supply of an excessive amount of flavor to a user. Also, it is possible to automatically stop the flavor inhaler 100, when the ability to release flavor components in the flavor source is remarkably degraded.

In a manner similar to that in above step S706, the judgment in above step S710 may be performed at any of timing 1) after a single puff action is completed, 2) during a predetermined time lag that is between a point in time when puff action is detected by the inhaling sensor 50 and a point in time when atomizing of aerosol is started, or 3) during puff action (during a period of electric conduction to the atomizing section 111R), for example.

In the case that judgment in step S710 is performed at timing after a single puff action is completed, an unnatural feel sensed by a user can be suppressed, since the control performed in step S712 does not interrupt atomizing of the aerosol during puff action of the user.

Note that the order of the judgment process in step S706 and the control process in step S708 following step S706, and the judgment process in step S710 and the control process in step S712 following step S710 may be changed between them and performed in the changed order.

Second Embodiment

In the following description, a second embodiment will be explained. In the following description, difference from the first embodiment will be explained.

A reference amount $A_R$ of aerosol is a amount of aerosol to be generated in the atomizing section 111R, and is defined by a pre-designed amount. More specifically, in the second embodiment, the reference amount $A_R$ of the aerosol is defined by a value that is obtained by dividing, by a pre-designed value $\beta'$, a designed value of a amount of the aerosol that should be passed through the first branched flow path 140A when a flow rate ratio coincides with the pre-designed value $\beta'$. In other words, the reference amount $A_R$ of the aerosol is made to be equal to the amount of the aerosol generated in the atomizing section 111R, so as to make the value of the amount of the aerosol to be passed though the first branched flow path 140A becomes the above designed value when a flavor unit 130 and/or an atomizing unit 111 having a flow rate ratio $\beta$ equal to the pre-designed value $\beta'$ are/is used.

A target amount $A_T$ of the aerosol is calculated based on the reference amount $A_R$ of the aerosol and the flow rate ratio $\beta$. In a tangible example, in the case that the flow rate ratio $\beta$ is larger than a pre-designed value $\beta'$, the target amount $A_T$ of the aerosol is set to be smaller than a target amount of the aerosol in the case that the flow rate ratio coincides with the pre-designed value $\beta'$; and, in the case that the flow rate ratio $\beta$ is smaller than the pre-designed value $\beta'$, the target amount $A_T$ of the aerosol is set to be larger than the target amount of the aerosol in the case that the flow rate ratio coincides with the pre-designed value $\beta'$.

In a tangible example, the target amount $A_T$ of the aerosol is set to a value that is obtained by dividing, by the flow rate ratio $\beta$, a product of the reference amount $A_R$ of the aerosol and the pre-designed value $\beta'$ of the flow rate ratio (i.e., $A_T = A_R * (\beta'/\beta)$). In such a case, the target amount $A_T$ of the aerosol is determined in such a manner that the amount of the aerosol flowing through the first branched flow path 140A per a single puff action is made to be constant regardless of the flow rate ratio $\beta$.

The control section 51 controls the atomizing section 111R in such as manner that the amount of the aerosol generated in the atomizing section 111R is made to be equal to the target amount $A_T$ of the aerosol.

Control of Electric Power Supplied to the Atomizing Section

Similar to the manner in the first embodiment, the control section 51 can calculate, based on a relational expression "$E_T = (A_T - b)/a$," a target amount $E_T$ of electric energy that is required for generating the target amount $A_T$ of the aerosol. That is, in the case that values of the characteristic parameters "a" and "b" have been known, the control section 51 can calculate the target amount $E_T$ of electric energy by use of the target amount $A_T$ of the aerosol in such a manner that a relational expression "$E_T = (A_T - b)/a$" is satisfied. Note that, regarding the parameters "a" and "b," explanation thereof is the same as the above explanation.

Thus, in the case that the target amount $A_T$ of the aerosol is determined based on the reference amount $A_R$ of aerosol and the flow rate ratio $\beta$ and by use of a relational expression "$A_T = A_R * \beta'/\beta$," the control section 51 can calculate the target amount $E_T$ of electric energy by use of the target amount $A_T$ of the aerosol in such a manner that a relational expression "$E_T = ((A_R * \beta'/\beta) - b)/a$" is satisfied. Except for change in the form of the mathematical formula for representing the target amount $E_T$ of electric energy, control of electric power for the atomizing section 111R is performed in a manner similar to that in the first embodiment.

Third Embodiment

In the following description, a third embodiment will be explained. In the following description, difference from the first embodiment will be explained.

In the first embodiment, the information source 134M in the flavor source 130 stores values relating to the flow rate ratio $\beta$. On the other hand, in the third embodiment, the information source 134M stores identification information associated with values relating to the flow rate ratio $\beta$.

Also, in the first embodiment, the information source 111M in the atomizing unit 111 stores characteristic parameters (a, b, $T_{MIN}$, $T_{MAX}$) of the atomizing unit 111, an electric resistance value (R) of the atomizing section (the resistance heating element) 111R, and so on. On the other hand, in the third embodiment, the information source 111 stores identification information associated with the above pieces of information.

Configuration Represented by Blocks

Figure 3:
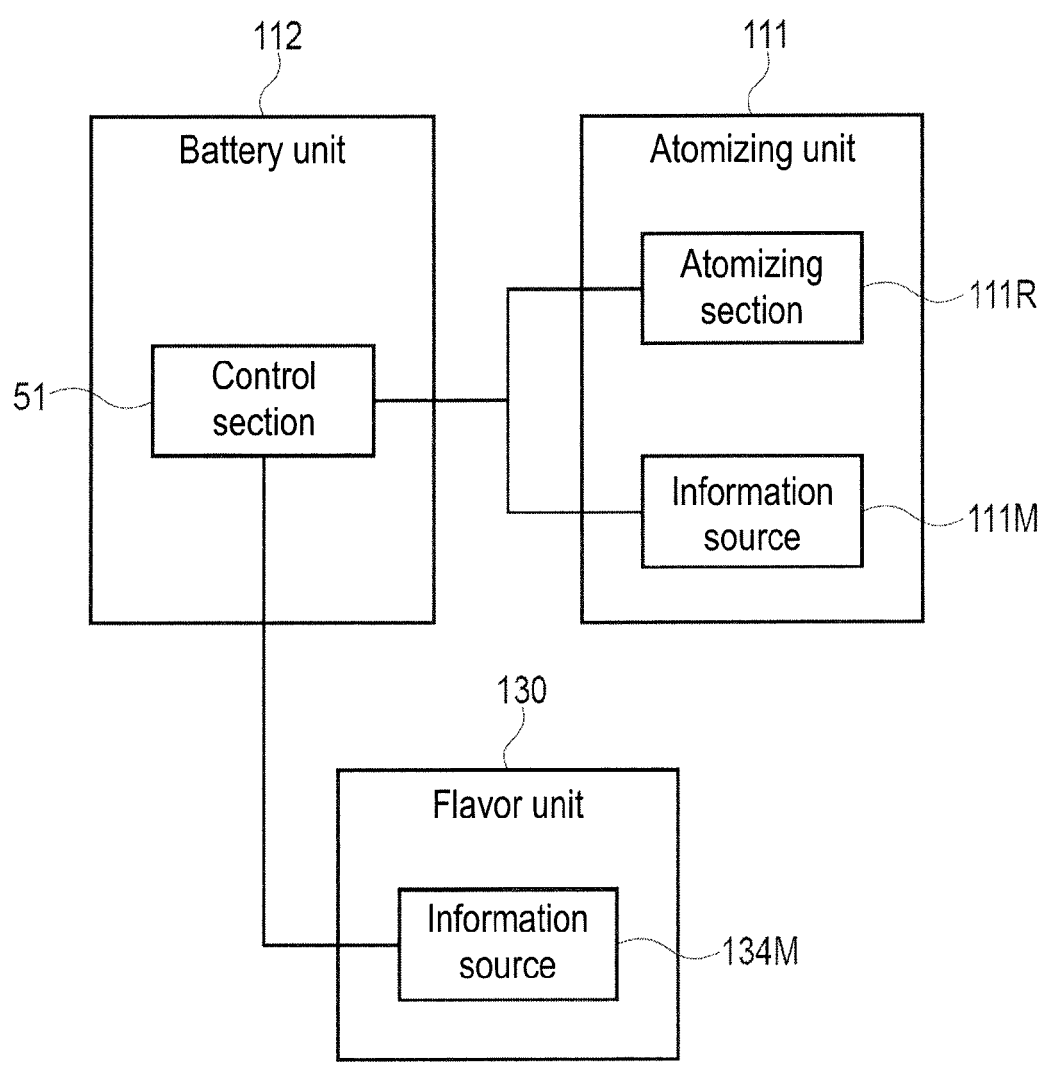
FIG. 3 is a figure showing, in a block diagram manner, a construction of a flavor inhaler.
Figure 8:
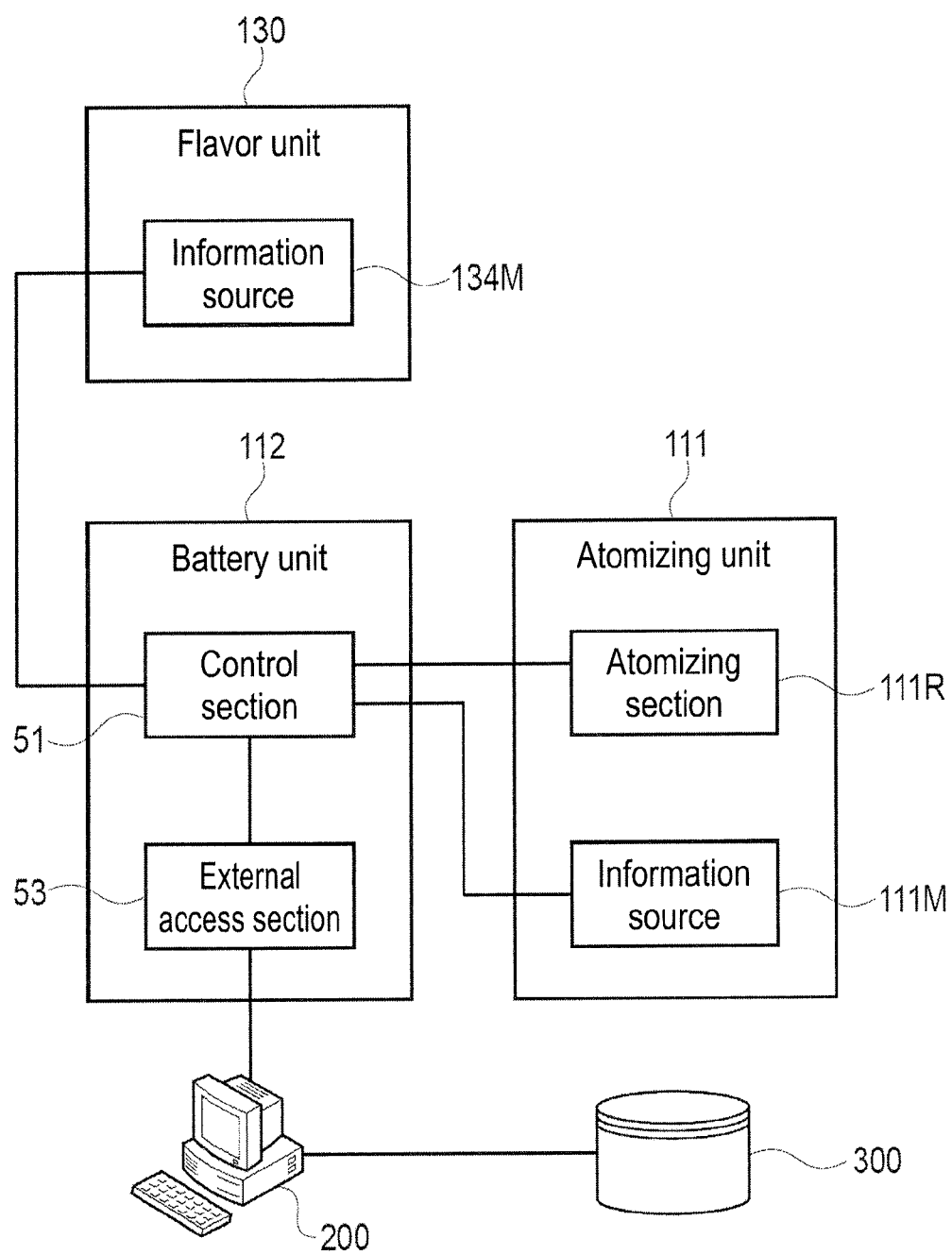
FIG. 8 is a figure showing, in a block diagram manner, a construction of a flavor inhaler according to a second embodiment.

In the following description, a block configuration of a flavor inhaler according to the second embodiment will be explained. FIG. 8 shows a block configuration of a flavor inhaler 100 according to the second embodiment. Note that, in FIG. 8, symbols similar to those shown in FIG. 3 are assigned to constructions similar to those shown in FIG. 3.

In FIG. 8, a communication terminal 200 is a terminal which has a function for communicating with a server 300. The communication terminal 200 comprises, for example, a personal computer, a smartphone, a tablet, or the like.

The server 300 comprises an external storage medium for storing values relating to the flow rate ratio $\beta$. The server 300 may further store characteristic parameters (a, b, $T_{MIN}$, $T_{MAX}$) of the atomizing unit 111, an electric resistance value (R) of the resistance heating element 111R, and so on. Further, as explained above, the information sources 134M and 111M store identification information associated with the above pieces of information.

As shown in FIG. 8, a control section 51 has a function for directly or indirectly accessing the server 300 via an external access section 53. In FIG. 8, a function by which the external access section 52 accesses the server 300 via the communication terminal 200 is shown as an example. In such a case, the external access section 53 may comprise, for example, a module for wired connection with the communication terminal 200 (for example, a USB port), or a module for wireless connection with the communication terminal 200 (for example, a Bluetooth (R) module or a NFC (Near Field Communication) module).

In this regard, the external access section 53 may has a function for directly communicating with the server 300. In such a case, the external access section 53 may comprise a wireless LAN module.

The communication terminal 200 reads identification information from the information sources 111M and/or 134M, and uses the read identification information for obtaining, from the server 300, information associated with the identification information, i.e., a value relating to a flow rate ratio β, characteristic parameters (a, b, $T_{MIN}$, $T_{MAX}$) of the atomizing unit 111, an electric resistance value (R) of the resistance heating element 111R, and so on. The value relating to the flow rate ratio β, the characteristic parameters (a, b, $T_{MIN}$, $T_{MAX}$) of the atomizing unit 111, the electric resistance value (R) of the resistance heating element 111R, and so on are sent from the communication terminal 200 to the control section 51 via the external access section 53.

The control section 51 can perform control of electric power supplied to the atomizing unit 111 in a manner explained above, based on the value relating to the flow rate ratio β, the characteristic parameters of the atomizing unit 111, and so on obtained from the server 300 via the communication terminal 200.

In the second embodiment, each of the information sources 111M and 134M comprises a memory. Meanwhile, an information source may comprise a barcode or an identification label that the atomizing unit 111 or the flavor unit 130 is provided with. Also, such a barcode or an identification label may be that given on an outside surface of the atomizing unit 111 or the flavor unit 130, on an operating manual packed with the atomizing unit 111 or the flavor unit 130, and/or on a box in which the atomizing unit 111 or the flavor unit 130 is packed, for example.

In the above case, the communication terminal 200 inputs identification information such as the barcode or the identification label or reading the identification information to thereby obtain information associated with the identification information, i.e., obtain the flow rate ratio β, the characteristic parameters (a, b, $T_{MIN}$, $T_{MAX}$) of the atomizing unit 111, the electric resistance value (R) of the resistance heating element 111R, and so on, from the server 300. The information obtained by the communication terminal 200 is sent to the control section 51 via the external access section 53.

In the case of the flavor inhaler according to the second embodiment, the control section 51 can obtain a correction value via the information source 134M, under the state that the flavor unit 130 is not attached to the atomizing unit 111, or the state that the cartridge comprising the flavor unit 130 and the atomizing unit 111 is not attached to the battery unit 112. In this regard, the control section 51 may be able to obtain a correction value, under the state that the flavor unit 130 is attached to the atomizing unit 111, or the state that the cartridge comprising the flavor unit 130 and the atomizing unit 111 is attached to the battery unit 112.

Calculation of the target amount $A_T$ of the aerosol may be performed right after obtaining the correction value, or at predetermined timing after obtaining the correction value. Regarding the predetermined timing at when calculation of the target amount $A_T$ of the aerosol is performed, explanation thereof is the same as that provided in the explanation of the first embodiment.

Although the embodiments of the present invention have been explained in the above description, the present invention is not limited to the embodiments, and the embodiments can be modified in various ways without departing from the scope of the gist of the present invention.

The invention claimed is:

1. A flavor inhaler comprising:
    an atomizing section for generating aerosol from an aerosol source;
    a flavor source positioned downstream the atomizing section;
    a mouthpiece section positioned downstream the flavor source;
    a control section for controlling the atomizing section;
    an aerosol flow path leading from the atomizing section to the mouthpiece section; and
    an information source for holding identification information associated with a correction value used for correcting a reference amount of the aerosol that is a amount of the aerosol to be generated in the atomizing section and is designed in advance; wherein
    the aerosol flow path is divided, in a part between the atomizing section and the flavor source, into a first branched flow path passing through the flavor source and a second branched flow path different from the first branched flow path;
    the correction value is a value relating to a flow rate ratio of a flow rate in the first branched flow path to a predetermined flow rate at the time when the mouthpiece section is sucked at the predetermined flow rate; and
    the control section controls the atomizing section based on a target amount of the aerosol that is calculated based on the reference amount of the aerosol and the correction value.

2. The flavor inhaler according to claim 1, wherein
    in the case that the flow rate ratio is larger than a pre-designed value, the target amount of the aerosol is set to be smaller than a target amount of the aerosol in the case that the flow rate ratio coincides with the pre-designed value; and
    in the case that the flow rate ratio is smaller than the pre-designed value, the target amount of the aerosol is set to be larger than the target amount of the aerosol in the case that the flow rate ratio coincides with the pre-designed value.

3. The flavor inhaler according to claim 1, wherein the first branched flow path and the second branched flow path are merged with each other in a point downstream the flavor source.

4. The flavor inhaler according to claim 1, wherein the control section controls supply of electric energy to the atomizing section.

5. The flavor inhaler according to claim 4, wherein
    the atomizing section comprises a resistance heating element; and
    electric energy supplied to the resistance heating element per a single puff action is represented by E,
    characteristic parameters of the atomizing section are represented by a and b,
    a amount of the aerosol generated per a single puff action is represented by A, and
    the control section calculates the amount A of the aerosol by use of formula A=a*E+b.

6. The flavor inhaler according to claim 4, wherein
    the atomizing section comprises a resistance heating element; and
    the target amount of the aerosol is represented by $A_T$,
    target electric energy that should be supplied to the resistance heating element per a single puff action is represented by $E_T$,
    characteristic parameters of the atomizing section are represented by a and b, and
    the control section determines the electric energy $E_T$ that should be supplied to the resistance heating element by use of formula $E_T=(A_T-b)/a$.

7. The flavor inhaler according to claim 5 comprising an information source having the characteristic parameters or identification information associated with the characteristic parameters.

8. The flavor inhaler according to claim 1, wherein the reference amount of the aerosol is defined by a designed value of a amount of the aerosol that should be passed through the first branched flow path when the flow rate ratio coincides with the pre-designed value.

9. The flavor inhaler according to claim 8, wherein the target amount of the aerosol is set to a value that is obtained by dividing the reference amount of the aerosol by the flow rate ratio.

10. The flavor inhaler according to claim 1, wherein the reference amount of the aerosol is defined by a value that is obtained by dividing, by the pre-designed value of the flow rate ratio, a designed value of a amount of aerosol that should be passed through the first branched flow path when the flow rate ratio coincides with the pre-designed value.

11. The flavor inhaler according to claim 10, wherein the target amount of the aerosol is set to a value that is obtained by dividing, by the flow rate ratio, a product of the reference amount of the aerosol and the pre-designed value.

12. The flavor inhaler according to claim 1 comprising:
an atomizing unit comprising the atomizing section and
a flavor unit comprising the flavor source, wherein
the flavor unit is constructed to be attachable/detachable to/from the atomizing unit.

13. The flavor inhaler according to claim 12, wherein the information source is positioned in the flavor unit.

14. The flavor inhaler according to claim 12, wherein the first branched flow path and the second branched flow path are positioned in the flavor unit.

15. The flavor inhaler according to claim 12, wherein calculation of the target amount of the aerosol is performed under a state that the flavor unit is being attached to the atomizing unit.

16. The flavor inhaler according to claim 15, wherein calculation of the target amount of the aerosol is performed when a state that the flavor unit is attached to the atomizing unit is detected.

17. The flavor inhaler according to claim 12, wherein calculation of the target amount of the aerosol is performed when predetermined manipulation performed by a user is detected.

18. The flavor inhaler according to claim 17 comprising an inhaling sensor for detecting inhaling action performed by a user, wherein
calculation of the target amount of the aerosol is performed when the inhaling action is detected by the inhaling sensor for the first time.

19. The flavor inhaler according to claim 12, wherein the control section reads the correction value via the information source, under a state that the flavor unit is being attached to the atomizing unit.

20. The flavor inhaler according to claim 12, wherein the control section reads the correction value via the information source, under a state that the flavor unit is not being attached to the atomizing unit.

21. The flavor inhaler according to claim 1, wherein, in the case that an accumulated value of amounts of the aerosol generated in the atomizing section or an accumulated value of amounts of the aerosol passed through the first branched flow path exceeds a first threshold value, the amount of the aerosol to be generated in the atomizing section is increased.

22. The flavor inhaler according to claim 1, wherein, in the case that an accumulated value of amounts of the aerosol generated in the atomizing section or an accumulated value of amounts of the aerosol passed through the first branched flow path exceeds a second threshold value, supply of electric power to the atomizing section is cut off.

23. The flavor inhaler according to claim 1 comprising a battery unit comprising a battery.

24. The flavor inhaler according to claim 23, wherein the battery unit is constructed to be attachable/detachable to/from the atomizing unit comprising the atomizing section.

25. The flavor inhaler according to claim 23, wherein the control section is positioned in the battery unit.

26. A cartridge comprising:
an atomizing section for generating aerosol from an aerosol source;
a flavor source positioned downstream the atomizing section;
a mouthpiece section positioned downstream the flavor source;
an aerosol flow path leading from the atomizing section to the mouthpiece section; and
an information source for holding identification information associated with a correction value used for correcting a reference amount of the aerosol that is a amount of the aerosol to be generated in the atomizing section and is designed in advance; wherein
the aerosol flow path is divided, in a part between the atomizing section and the flavor source, into a first branched flow path passing through the flavor source and a second branched flow path different from the first branched flow path; and
the correction value is a value relating to a flow rate ratio of a flow rate in the second branched flow path to a predetermined flow rate at the time when the mouthpiece section is sucked at the predetermined flow rate.

27. A flavor unit attachable/detachable to/from an atomizing unit comprising an atomizing section for generating aerosol, wherein the flavor unit comprising:
a flavor source;
a mouthpiece section positioned downstream the flavor source;
an aerosol flow path which is constructed to be able to communicate with the atomizing section in the atomizing unit and leads to the mouthpiece section; and
an information source for holding identification information associated with a correction value used for correcting a reference amount of aerosol that is a amount of the aerosol to be generated in the atomizing section and is designed in advance; wherein
the aerosol flow path is divided, in a part between the atomizing section and the flavor source, into a first branched flow path passing through the flavor source and a second branched flow path different from the first branched flow path; and
the correction value is a value relating to a flow rate ratio of a flow rate in the second branched flow path to a predetermined flow rate at the time when the mouthpiece section is sucked at the predetermined flow rate.

* * * * *